(12) United States Patent
Lee

(10) Patent No.: US 8,624,618 B2
(45) Date of Patent: Jan. 7, 2014

(54) APPARATUS AND METHOD FOR INSPECTING CIRCUIT OF SUBSTRATE

(75) Inventor: Seung Seoup Lee, Gyunggi-do (KR)

(73) Assignee: Samsung Electro-Mechanics Co., Ltd., Suwon, Gyunggi-do (KR)

( * ) Notice: Subject to any disclaimer, the term of this patent is extended or adjusted under 35 U.S.C. 154(b) by 290 days.

(21) Appl. No.: 12/710,149

(22) Filed: Feb. 22, 2010

(65) Prior Publication Data

US 2011/0109339 A1    May 12, 2011

(30) Foreign Application Priority Data

Nov. 12, 2009    (KR) .......................... 10-2009-0109306

(51) Int. Cl.
*G01R 31/00*    (2006.01)

(52) U.S. Cl.
USPC .................. 324/756.04; 324/762.01; 324/713

(58) Field of Classification Search
USPC .................. 324/760.01, 763.01, 762.05, 537, 324/756.04, 762.01, 713, 755.11; 382/141; 345/107; 73/49.3, 52
See application file for complete search history.

(56) References Cited

U.S. PATENT DOCUMENTS

| | | | | | |
|---|---|---|---|---|---|
| 4,125,805 | A | * | 11/1978 | Nagamatsu et al. | 324/558 |
| 4,507,605 | A | * | 3/1985 | Geisel | 324/536 |
| 4,914,395 | A | * | 4/1990 | Hamada | 324/557 |
| 6,392,786 | B1 | * | 5/2002 | Albert | 359/296 |
| 6,634,216 | B1 | * | 10/2003 | Yasumoto | 73/49.3 |
| 6,639,580 | B1 | * | 10/2003 | Kishi et al. | 345/107 |
| 6,751,008 | B2 | * | 6/2004 | Liang et al. | 359/296 |
| 6,788,450 | B2 | * | 9/2004 | Kawai et al. | 359/296 |
| 2004/0119680 | A1 | * | 6/2004 | Daniel et al. | 345/107 |
| 2006/0087327 | A1 | * | 4/2006 | Ueno et al. | 324/713 |
| 2007/0070030 | A1 | * | 3/2007 | Zang et al. | 345/107 |
| 2008/0024426 | A1 | * | 1/2008 | Chopra et al. | 345/107 |
| 2008/0169821 | A1 | * | 7/2008 | Wang et al. | 324/537 |
| 2008/0259021 | A1 | * | 10/2008 | Choi et al. | 345/107 |
| 2009/0009465 | A1 | * | 1/2009 | Choi et al. | 345/107 |

FOREIGN PATENT DOCUMENTS

| | | |
|---|---|---|
| JP | 45-000625 | 10/1967 |
| JP | 2002-139749 | 5/2002 |
| JP | 2003-084025 | 3/2003 |
| JP | 2003-107120 | 4/2003 |
| JP | 2003-171447 | 6/2003 |

(Continued)

OTHER PUBLICATIONS

Machine Translation of JP2006-023089A.*

(Continued)

*Primary Examiner* — Arleen M Vazquez
(74) *Attorney, Agent, or Firm* — Blakely, Sokoloff, Taylor & Zafman LLP

(57) ABSTRACT

An apparatus and method for inspecting a circuit of a substrate is described. The apparatus includes a pin probe coming into contact with a first end of an electrode formed on a first side of a substrate, a voltage source for applying a voltage to the pin probe, a film disposed at a second end of the electrode formed on a second side of the substrate, a dielectric fluid sealed in the film, and an electronic ink dispersed in the dielectric fluid, and charged with electricity to flow when the electrode is electrified. The present invention is advantageous in that whether an electrode has been electrified is measured using charged electronic ink, so that the use of a pin probe is limited to one side of a substrate, thus reducing cost required for the entire inspection.

21 Claims, 12 Drawing Sheets

(56) References Cited

FOREIGN PATENT DOCUMENTS

| JP | 2006-023089 | | 1/2006 |
|---|---|---|---|
| JP | 2006023089 A | * | 1/2006 |
| JP | 2006-349767 | | 12/2006 |

OTHER PUBLICATIONS

Office Action from counterpart Japanese Patent Application No. 10-2010-035252, mailed Jun. 26, 2012, 5 pages, English Summary included.

* cited by examiner

APPARATUS AND METHOD FOR INSPECTING CIRCUIT OF SUBSTRATE

CROSS REFERENCE TO RELATED APPLICATION

This application claims the benefit of Korean Patent Application No. 10-2009-0109306, filed on Nov. 12, 2009, entitled "Inspection Apparatus and Method For Circuit of Substrate", which is hereby incorporated by reference in its entirety into this application.

BACKGROUND OF THE INVENTION

1. Technical Field

The present invention relates to an apparatus and method for inspecting the circuit of a substrate.

2. Description of the Related Art

With the recent development of the electronics industry, the requirement that electronic parts be of high functionality has rapidly increased, and thus inspection methods for the circuit of a substrate, performed when the substrate is manufactured, also require high precision, high speed and low cost. However, methods for inspecting the circuit of a substrate, which are currently being generally used, that is, contact pin probe methods, do not yet satisfy the above requirements.

FIG. 1 is a sectional view showing a conventional apparatus for inspecting the circuit of a substrate using contact pin probes.

Referring to FIG. 1, the apparatus for inspecting the circuit of a substrate 15 using contact pin probes includes two pin probes 11 and 12, a voltage source 13, and an ammeter 14.

The first pin probe 11 comes into contact with one end of an electrode 16, formed on one side of the substrate 15, and functions to transfer current supplied by a voltage source 13 to the electrode 16. The second pin probe 12 comes into contact with the other end of the electrode 16, formed on the other side of the substrate 15, and functions to receive current from the electrode 16 and transfer the current to the ammeter 14.

That is, when the electrode 16 is electrified, the voltage source 13, the first pin probe 11, the electrode 16, the second pin probe 12, and the ammeter 14 are sequentially connected in series, so that a closed circuit is formed and current flows into the closed circuit. Therefore, when current is measured using the ammeter 14, a resistance value can be obtained using Ohm's law (R=V/I). When the electrode 16 is electrified, a resistance of 0Ω must be theoretically measured. However, since conducting wires, forming the pin probes 11 and 12 and the closed circuit, have their own resistances, the resistance is measured as a relatively small value and not 0Ω.

Meanwhile, when the electrode 16 is not electrified, current does not flow, and the resistance becomes infinite (V/0=∞).

Therefore, the apparatus for inspecting the circuit of a substrate using pin probes can determine whether the electrode has been electrified by measuring the resistance value.

However, the conventional apparatus for inspecting the circuit of a substrate is problematic because pin probes must be precisely manufactured to cope with the micro-patterning of a substrate, so that the cost of manufacturing pin probes gradually increases, and thus the entire cost required for inspection also increases.

Further, when defects in which an electrode pad has become slightly unfastened and then the electrode is not electrified are present, the electrode may be electrified due to the pressure of pin probes at the time of inspecting the circuit, and thus the results of an erroneous measurement indicating that the electrode is normal may be obtained.

Furthermore, the conventional apparatus is problematic in that, since pin probes must be brought into contact with both ends of the electrode, respectively, measurement time increases, and in that, since heat is generated by the flow of current during the inspection, the electrode may be broken down.

SUMMARY OF THE INVENTION

Accordingly, the present invention has been made keeping in mind the above problems occurring in the prior art, and the present invention is intended to provide an apparatus and method for inspecting the circuit of a substrate, which utilize electrophoresis for inspecting the circuit of a substrate, so that erroneous measurements can be prevented even when electrode pads have become slightly unfastened, and which use pin probes only on one side of the substrate, so that the cost of inspection caused by the consumption of pin probes can be reduced.

In accordance with an aspect of the present invention, there is provided an apparatus for inspecting a circuit of a substrate, comprising a pin probe coming into contact with a first end of an electrode formed on a first side of a substrate, a voltage source for applying a voltage to the pin probe, a film disposed at a second end of the electrode formed on a second side of the substrate, a dielectric fluid sealed in the film, and an electronic ink dispersed in the dielectric fluid, and charged with electricity to flow when the electrode is electrified.

In an embodiment, the film comprises a plurality of micro capsules, in which the dielectric fluid and the electronic ink are sealed.

In an embodiment, the film comprises partitions which are vertically formed so that the electronic ink is separated at regular intervals.

In an embodiment, the voltage source applies a positive voltage to the pin probe, and the electronic ink is charged with negative electricity.

In an embodiment, the voltage source applies a negative voltage to the pin probe, and the electronic ink is charged with positive electricity.

In an embodiment, the electronic ink includes white ink and black ink

In an embodiment, the white ink is charged with positive electricity, and the black ink is charged with negative electricity.

In an embodiment, the white ink is charged with negative electricity, and the black ink is charged with positive electricity.

In an embodiment, the film is made of polyethylene terephthalate (PET), poly carbonate (PC), polymethyl methacrylate (PMMA), polyethylene naphthalate (PEN), polyethersulfone (PES), cyclic olefin copolymer (COC), glass, or tempered glass.

In an embodiment, the dielectric fluid is transparent

In an embodiment, the electronic ink and the dielectric fluid have identical specific gravities.

In an embodiment, the apparatus further comprise a camera for capturing an image indicating whether the electronic ink is flowing.

In an embodiment, the apparatus further comprise image comparison means for comparing the image captured by the camera with a comparative image, obtained when the electrode is electrified, thus determining whether the electrode has been electrified.

In an embodiment, the substrate is a Printed Circuit Board (PCB) or a semiconductor wafer.

In accordance with another aspect of the present invention, there is provided a method of inspecting a circuit of a substrate, comprising (A) preparing a pin probe and a film in which dielectric fluid in which electronic ink is dispersed is sealed, (B) bringing the pin probe into contact with a first end of an electrode formed on a first side of a substrate and disposing the film at a second end of the electrode formed on a second side of the substrate, and (C) measuring whether the electronic ink, which is charged when a voltage source applies a voltage to the pin probe, is flowing, thus determining whether the electrode has been electrified.

In an embodiment, at (C), the electronic ink flows when the electrode is electrified.

In an embodiment, (C) is performed to capture an image using a camera, thus determining whether the electronic ink is flowing.

In an embodiment, (C) is performed to compare, using image comparison means, the image captured by the camera with a comparative image, obtained when the electrode is electrified, thus determining whether the electrode has been electrified.

In an embodiment, at (A), the electronic ink and the dielectric fluid have identical specific gravities, and at (C), the voltage source applies the voltage to the pin probe only until flow of the electronic ink stops.

DESCRIPTION OF THE PREFERRED EMBODIMENTS

Figure 1:
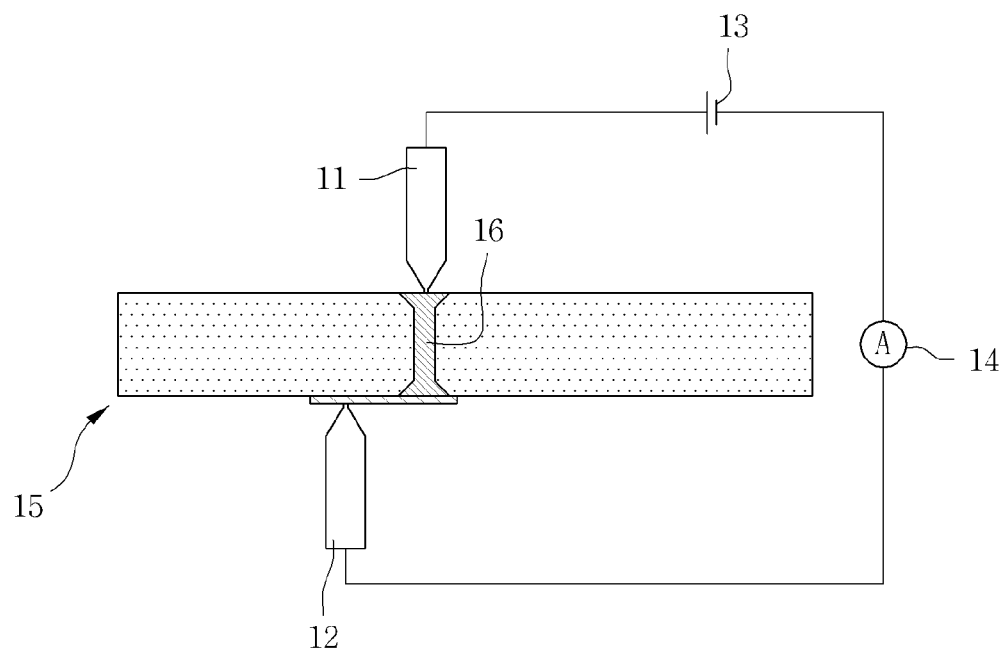
FIG. 1 is a sectional view showing a conventional apparatus for inspecting the circuit of a substrate using contact pin probes.

Prior to giving the description, the terms and words used in the present specification and claims should not be interpreted as being limited to their typical meaning based on the dictionary definitions thereof, but should be interpreted to have the meaning and concept relevant to the technical spirit of the present invention, on the basis of the principle by which the inventor can suitably define the implications of terms in the way which best describes the invention.

The above and other objects, features and advantages of the present invention will be more clearly understood from the following detailed description taken in conjunction with the accompanying drawings. In the present specification, reference now should be made to the drawings, in which the same reference numerals are used throughout the different drawings to designate the same or similar components. Further, the terms "one side", "the other side", "one end" and "the other end" are used to distinguish one component from the other component, and the components of the present invention are not limited by the terms. Further, in the description of the present invention, if detailed descriptions of related well-known constructions or functions are determined to make the gist of the present invention unclear, the detailed descriptions will be omitted.

Hereinafter, embodiments of the present invention will be described in detail with reference to the attached drawings.

Figure 2A:
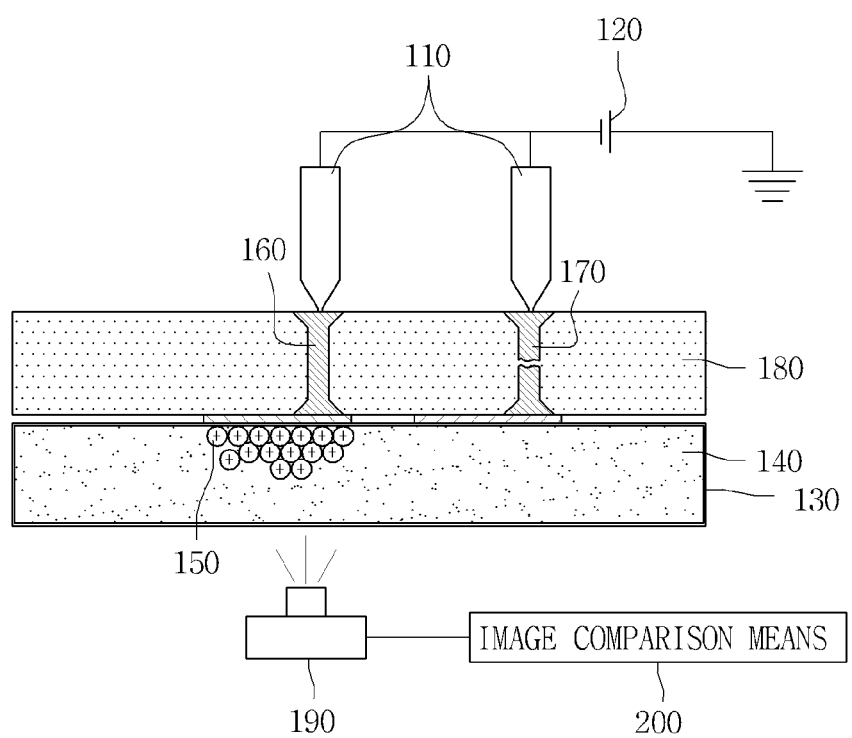
FIGS. 2A and 2B are sectional views showing an apparatus for inspecting the circuit of a substrate according to a first embodiment of the present invention.
Figure 2B:
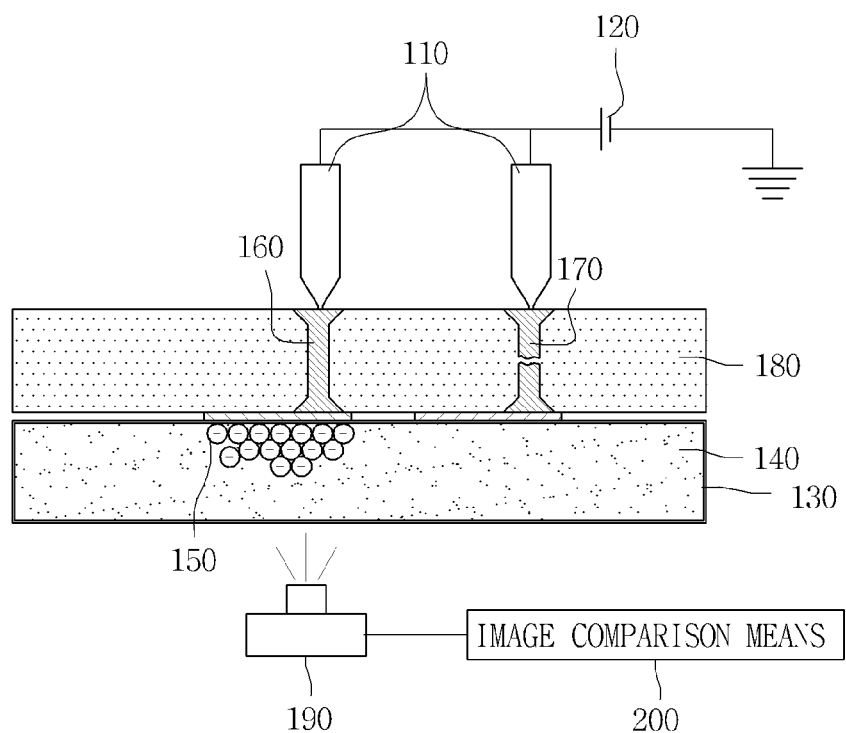

FIGS. 2A and 2B are sectional views showing an apparatus for inspecting the circuit of a substrate according to a first embodiment of the present invention.

As shown in FIGS. 2A and 2B, the apparatus for inspecting the circuit of a substrate 180 according to the present embodiment includes a pin probe 110 coming into contact with one end of an electrode 160 formed on one side of the substrate 180, a voltage source 120 for applying a voltage to the pin probe 110, a film 130 disposed at the other end of the electrode 160 formed on the other side of the substrate 180, a dielectric fluid 140 sealed in the film 130, and electronic ink 150 dispersed in the dielectric fluid 140 and charged with electricity to flow when the electrode 160 is electrified. The apparatus for inspecting the circuit of the substrate 180 according to the present embodiment may further include a camera 190 for capturing an image indicating whether the electronic ink 150 is flowing, and an image comparison means 200 for comparing the image captured by the camera 190 with a comparative image obtained when the electrode 160 is electrified, thus determining whether the electrode 160 has been electrified.

Here, electrodes 160 and 170 are targets to be inspected by the apparatus for inspecting the circuit of the substrate 180 according to the present invention, and indicate a concept including via holes, circuit layers and pads which are vertically formed through the substrate 180 and are exposed on both sides of the substrate 180. Further, in the present embodiment, the substrate 180 is shown as a single layer, but it is apparent that a multi-layer substrate is included in the scope of the present invention, and the substrate is a concept including a Printed Circuit Board (PCB) or a semiconductor wafer.

A pin probe 110 comes into contact with one end of each of the electrodes 160 and 170 formed on one side of the substrate 180 and function to transfer the voltage applied by the voltage source 120 to the electrodes 160 and 170. In the electrode 160 receiving the voltage, an electric field is generated. Whether the electrodes 160 and 170 have been electrified can be measured using such an electric field. This operation will be described in detail later.

Further, such a pin probe 110 is manufactured using a microscopic pin-type structure to cope with fine circuits. The cross section of the pin probe 110 typically has a circular shape, but is not limited to such a shape and may have the shape of a polygon, such as a triangle or a rectangle. Further, the pin probe 110 is implemented as a conductor to transfer the voltage to the electrodes 160 and 170. The surface of the pin probe 110 is plated with metal having low electric resistance and high surface hardness, for example, a precious metal such as gold or rhodium, so as to minimize the electric resistance of the pin probe 110 itself.

The voltage source 120 functions to apply a voltage to the pin probe 110. In this case, the voltage source 120 is preferably implemented as a DC voltage source 120 for applying a voltage of 70V to 100V, but is not limited to that voltage source, and a voltage source 120 for applying a suitable voltage in consideration of the thickness of the substrate 180, the weight of the electronic ink 150, etc. may be selected as the voltage source 120.

The film 130 is a means for sealing the dielectric fluid 140, which will be described later, and is disposed on the other side of the substrate 180, which is opposite one side of the substrate 180 on which the pin probe 110 is disposed. The film 130 may be made of polyethylene terephthalate (PET), Poly Carbonate (PC), polymethyl methacrylate (PMMA), Polyethylene Naphthalate (PEN), polyethersulfone (PES), cyclic olefin copolymer (COC), glass, tempered glass, etc. Further, the dielectric fluid 140 and the electronic ink 150 which are core components of the present invention are scarcely influenced by the bending of the film 130. Therefore, according to the circumstances, the film 130 may be flexibly manufactured.

The dielectric fluid 140 is a dispersion medium sealed in the film 130 and functions to allow the electronic ink 150, which is a dispersoid dispersed in the dielectric fluid 140, to flow through the fluid 140. The dielectric fluid 140 may be typically implemented using a fluid exhibiting a color (dyed colloidal suspension), such as polydimethylsiloxane (PDMS) oil, but may be implemented using a transparent fluid to more definitely measure the flow of the electronic ink 150.

The electronic ink 150 is composed of corpuscles dispersed in the dielectric fluid 140 as minute particles, and is configured to be charged with positive electricity or negative electricity and to flow through the dielectric fluid when the electrode 160 or 170 is electrified, thus making it possible to visually (with the naked eye or the camera 190) determine whether the electrodes 160 and 170 have been electrified. In more detail, a procedure for allowing the electric ink 150 to flow will be described below. That is, the voltage from the pin probes 110 is applied to the electrodes 160 and 170. Since the other end of each of the electrodes 160 and 170 is open, current does not flow through the other end. An electric field is generated at the other end of the electrified electrode 160. The electronic ink 150 flows owing to the electric field generated at the other end of the electrified electrode 160.

For example, as shown in FIG. 2A, when the voltage source 120 applies a negative voltage to the pin probes 110, the electronic ink 150 charged with positive electricity flows to the other end of the electrified electrode 160 due to electrical attractive force, but does not flow to the other end of the unelectrified electrode 170.

Further, as shown in FIG. 2B, when the voltage source 120 applies a positive voltage to the pin probes 110, the electronic ink 150 charged with negative electricity flows to the other end of the electrified electrode 160 due to electrical attractive force, but does not flow to the other end of the unelectrified electrode 170.

Therefore, it can be determined that the electrode 160 to which the electronic ink 150 flows is electrified, and that the electrode 170 to which the electronic ink 150 does not flow is not electrified. That is, whether the electrode 160 has been electrified can be determined using electrophoresis.

As described above, the apparatus for inspecting the circuit of the substrate according to the present invention performs inspection using electrophoresis which is a non-contact measurement method, without bringing the pin probe 110 into contact with the other end of each of the electrodes 160 and 170, so that the use of the pin probes 110 can be reduced, and thus the entire inspection cost and inspection time can be decreased. Further, erroneous measurements that may occur when the pads of the electrodes have become slightly unfastened in a contact measurement method can be prevented. Furthermore, since current does not flow through the electrodes 160 and 170 during inspection, the breakdown of the electrodes 160 and 170 can be prevented.

Meanwhile, the case where the voltage source 120 applies a positive voltage to the pin probes 110 and the electronic ink 150 is charged with positive electricity, or the case where the voltage source 120 applies a negative voltage to the pin probes 110 and the electronic ink 150 is charged with negative electricity can also be taken into account. However, in this case, the electronic ink 150 becomes more distant from the other end of the electrified electrode 160 due to electrical repulsive force. As a result, a problem arises in that determination of whether the electrode 160 has been electrified cannot be definitely performed. Therefore, it is preferable that, as described above, the electronic ink 150 be charged with electricity which is opposite that of the voltage applied by the voltage source 120 to the pin probes 110.

Further, at the time of determining based on the flow of the electronic ink 150 whether the electrode 160 has been electrified, power can be reduced using bi-stability. The term 'bi-stability' means a property that, after the electronic ink 150 flows due to an electric field and collects around the other end of the electrode 160, the electronic ink 150 does not move even if the electric field is eliminated Bi-stability is desirably implemented when the specific gravity of a dispersoid is equal to that of a dispersion medium. Accordingly, it is preferable that the specific gravities of the electronic ink 150 and the dielectric fluid 140 be identical to each other. However, the term 'identical specific gravity' does not mean perfect identicalness in a mathematical meaning, but is a concept including errors in the manufacturing process of the electronic ink 150 or the dielectric fluid 140.

Meanwhile, titanium dioxide or carbon may preferably be used as the electronic ink 150. The size of the electronic ink 150 is not especially limited, but may preferably be 1 to 2 μm so that measurement is facilitated while the flow of the electronic ink 150 caused by electrical attractive force is possible.

Meanwhile, the flow of the electronic ink 150 can be measured with the naked eye, but the camera 190 for capturing an image indicating whether the electronic ink 150 is flowing is preferably provided to perform more precise measurement. Further, it is more preferable to provide the image comparison means 200 for comparing the image captured by the camera 190 with a previously input comparative image, obtained when the electrode is electrified, and then precisely determining whether the electrode 160 has been electrified.

Figure 3A:
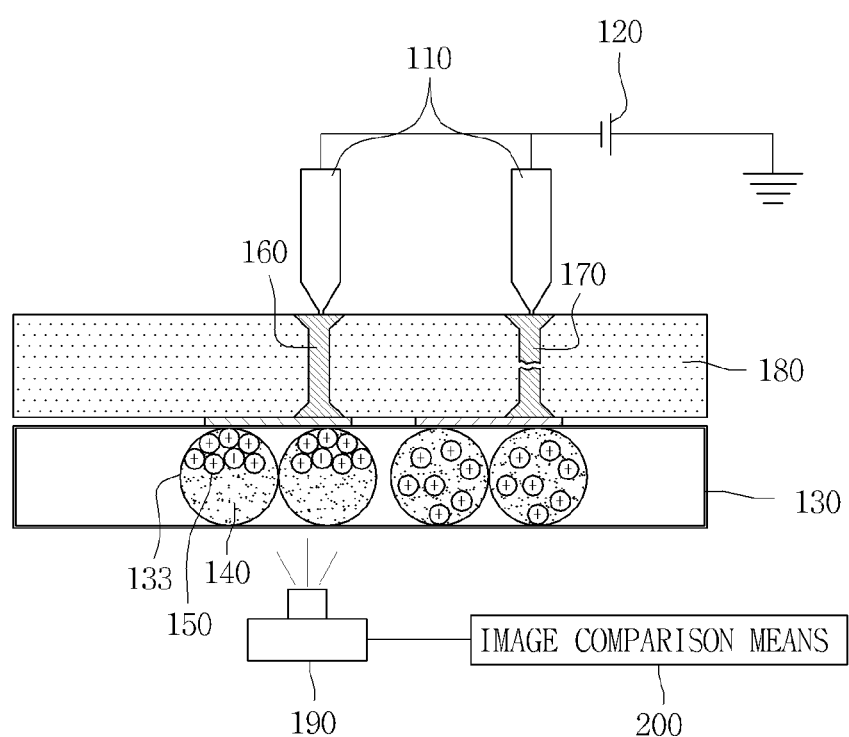
FIGS. 3A and 3B are sectional views showing an apparatus for inspecting the circuit of a substrate according to a second embodiment of the present invention.
Figure 3B:
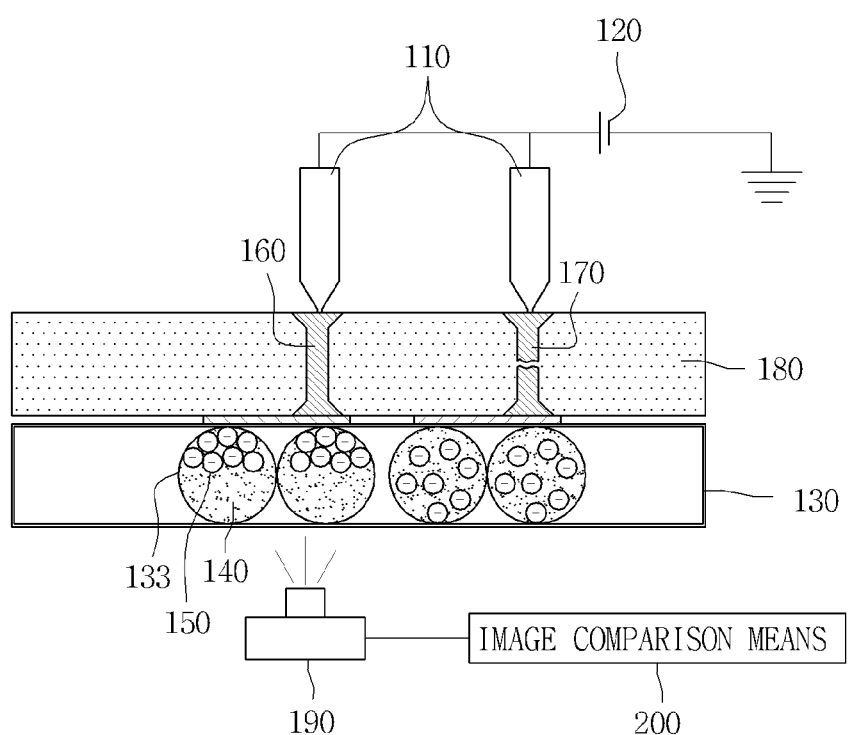

FIGS. 3A and 3B are sectional views showing an apparatus for inspecting the circuit of a substrate according to a second embodiment of the present invention.

When the present embodiment is compared with the above-described first embodiment, the largest difference therebetween is that micro capsules 133 in which a dielectric fluid 140 and electronic ink 150 are sealed are further included in a film 130. Components other than the micro capsules 133 are identical to those of the above embodiment, and thus a repetitive description thereof will be omitted, and the micro capsules 133, which indicate the difference, will be described in detail.

In the first embodiment, since the electronic ink 150 can freely flow into the entire space of the inside of the film 130, the electronic ink 150 may cluster or cohere. In this case, problems may arise in that, even if electrical attractive force acts on the electronic ink 150, the electronic ink 150 may not flow, or in that, since the densities of portions of the electronic ink 150 differ, it is difficult to precisely measure the flow of the electronic ink 150.

In order to solve the above problems, the present embodiment employs the micro capsules 133. Each of the micro capsules 133 defines a space in which the electronic ink 150 can flow, thus preventing the electronic ink 150 from clustering or cohering on a specific portion. Further, when the micro capsules 133 are minutely manufactured, the apparatus of the present invention has an advantage in that measurement resolution can be improved, thus coping with the micro-patterning of the substrate 180.

Even in the present embodiment, similarly to the above first embodiment, the voltage source 120 applies a negative voltage to the pin probes 110 and allows the electronic ink 150 to be charged with positive electricity, so that whether the electrodes 160 and 170 have been electrified can be measured (refer to FIG. 3A). Alternatively, the voltage source 120 applies a positive voltage to the pin probes 110 and allows the electronic ink 150 to be charged with negative electricity, so that whether the electrodes 160 and 170 have been electrified can be measured (refer to FIG. 3B).

Figure 4A:
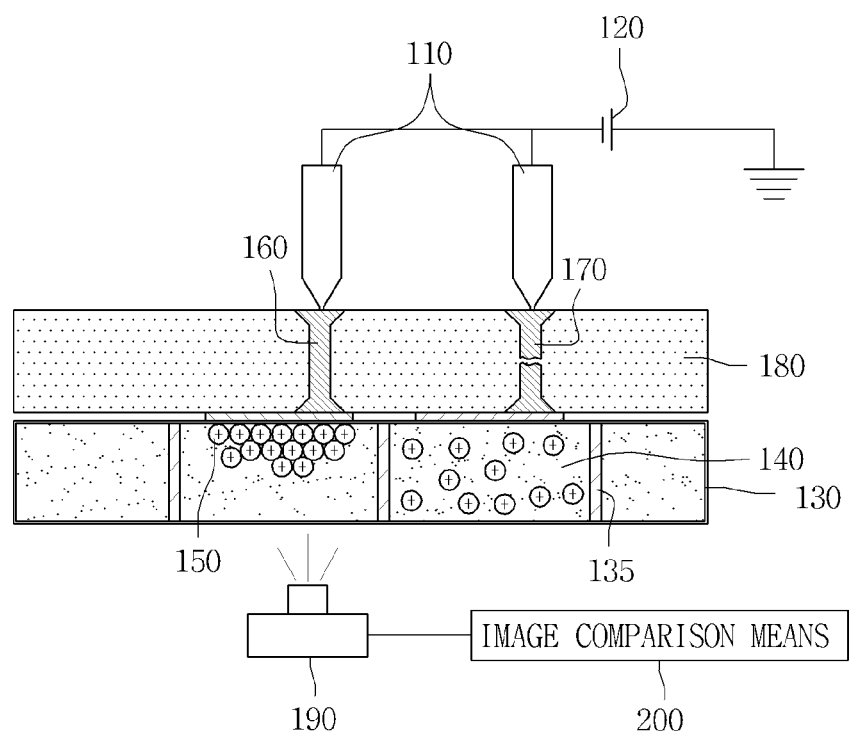
FIGS. 4A and 4B are sectional views showing an apparatus for inspecting the circuit of a substrate according to a third embodiment of the present invention.
Figure 4B:
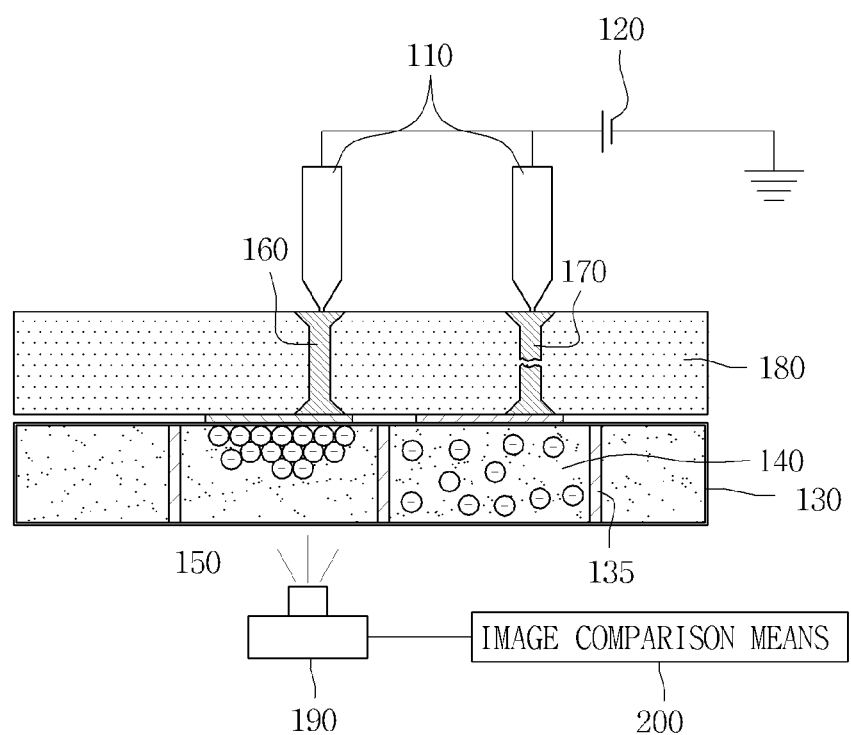

FIGS. 4A and 4B are sectional views of an apparatus for inspecting the circuit of a substrate according to a third embodiment of the present invention.

When the present embodiment is compared with the above-described embodiments, the largest difference therebetween is that partitions 135 are vertically formed in a film 130 so that electronic ink 150 is separated at regular intervals. Components other than the partitions 135 are identical to those of the above embodiments, and thus a repetitive description thereof will be omitted, and the partitions, which indicate the difference, will be described in detail.

The partitions 135 of the present embodiment perform a function similar to that of the micro capsules 133 of the second embodiment. That is, the partitions 135 provided in the film 130 define spaces in which the electronic ink 150 can flow, thus preventing the electronic ink 150 from clustering or cohering on a specific portion. Further, when the partitions 135 are formed at regular minute intervals, the apparatus of the present invention has an advantage in that measurement resolution can be improved, thus coping with the micro-patterning of the substrate 180. Moreover, since the partitions 135 function to support the film 130, the thickness of the film 130 can be prevented from being formed to be non-uniform.

Even in the present embodiment, similarly to the above first embodiment, the voltage source 120 applies a negative voltage to the pin probes 110 and allows the electronic ink 150 to be charged with positive electricity, so that whether the electrodes 160 and 170 have been electrified can be measured (refer to FIG. 4A). Alternatively, the voltage source 120 applies a positive voltage to the pin probes 110 and allows the electronic ink 150 to be charged with negative electricity, so that whether the electrodes 160 and 170 have been electrified can be measured (refer to FIG. 4B).

Figure 5A:
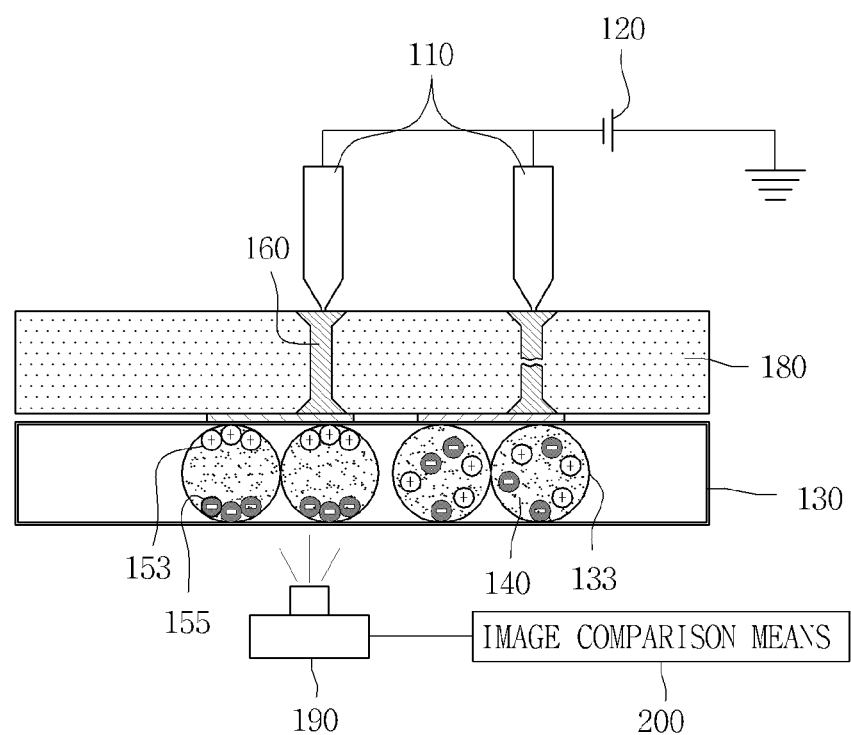
FIGS. 5A and 5B are sectional views showing an apparatus for inspecting the circuit of a substrate according to a fourth embodiment of the present invention.
Figure 5B:
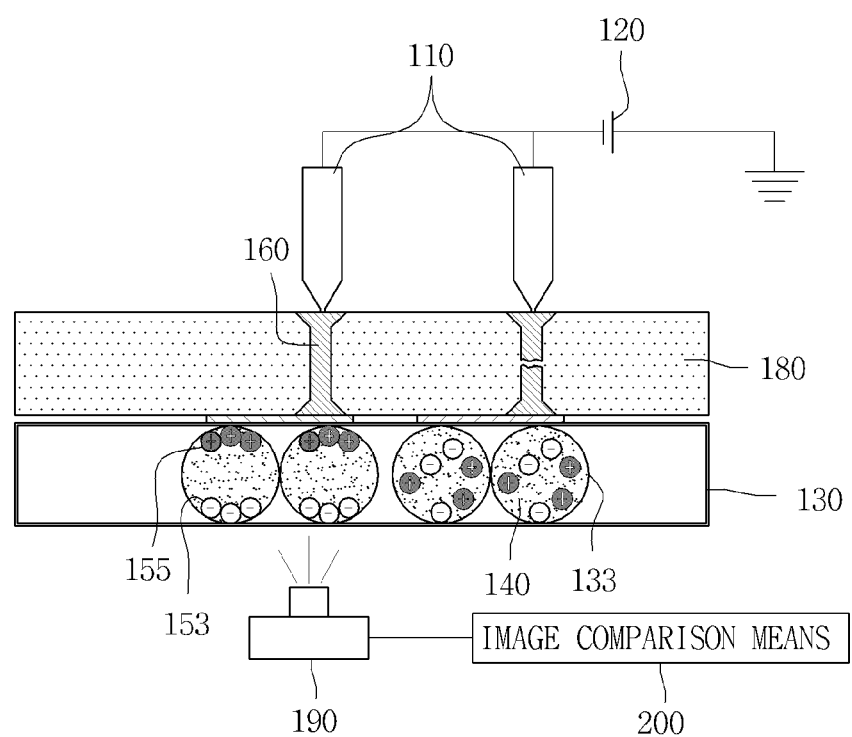

FIGS. 5A and 5B are sectional views showing an apparatus for inspecting the circuit of a substrate according to a fourth embodiment of the present invention.

When the present embodiment is compared with the above embodiments, the largest difference therebetween is that electronic ink 150 is composed of white ink 153 and black ink 155. Further, the white ink 153 and the black ink 155 are separated from each other when they are charged with electricity having different polarities and electric fields act on each other. Therefore, the flow of the electronic ink 150 can be more definitely measured.

For example, as shown in FIG. 5A, when the white ink 153 is charged with positive electricity, and the black ink 155 is charged with negative electricity, and thereafter the voltage source 120 applies a negative voltage to the pin probes 110, the white ink 153 moves to the other end of the electrified electrode 160 due to electrical attractive force, and the black ink 155 becomes more distant from the other end of the electrified electrode 160 due to electrical repulsive force, and thus the white ink 153 and the black ink 155 become separated from each other. In contrast, since an electric field is not generated at the other end of the unelectrified electrode 170, the white ink 153 and the black ink 155 are not separated from each other.

Further, as shown in FIG. 5B, when the white ink 153 is charged with negative electricity and the black ink 155 is charged with positive electricity, and thereafter the voltage source 120 applies a negative voltage to the pin probes 110, the black ink 155 moves to the other end of the electrified electrode 160 due to electrical attractive force, and the white ink 153 becomes more distant from the other end of the electrode 160 due to electrical repulsive force, and thus the white ink 153 and the black ink 155 are separated from each other. In contrast, since an electric field is not generated at the other end of the unelectrified electrode 170, the white ink 153 and the black ink 155 do not become separated from each other.

Therefore, in the present embodiment, whether the electrode 160 has been electrified can be precisely determined based on the determination of whether the white ink 153 and the black ink 155 have been separated from each other by using the white ink 153 and the black ink 155 which are definitely distinguished from each other.

FIGS. 5A and 5B show the case where the micro capsules 133 are also employed (refer to the second embodiment), but the present invention is not limited to this embodiment. That is, the electronic ink 150 may be composed of white ink 153 and black ink 155 even when only the above basic film 130 is provided (refer to the first embodiment) and when the film 130 equipped with partitions is provided (refer to the third embodiment).

FIGS. 6 to 10 are sectional views sequentially showing a method of inspecting the circuit of a substrate according to an embodiment of the present invention.

As shown in FIGS. 6 to 10, the method of inspecting the circuit of a substrate according to the present embodiment includes (A) preparing both a pin probe 110 and a film 130 in which a dielectric fluid 140, in which electronic ink 150 is dispersed, is sealed, (B) bringing the pin probe 110 into contact with one end of an electrode 160 formed on one side of a substrate 180, and disposing the film 130 at the other end of the electrode 160 formed on the other side of the substrate 180, and (C) a voltage source 120 applying a voltage to the pin probe 110 and measuring whether charged electronic ink 150 is flowing, thus determining whether the electrode 160 has been electrified.

The method of inspecting the circuit of a substrate according to the present embodiment is implemented using the above-described apparatus for inspecting the circuit of a substrate. Since the components of the apparatus for inspecting the circuit of a substrate have already been described, a repetitive description thereof will be omitted, and a description will be made on the basis of the time-series properties of the method of inspecting the circuit of the substrate.

Figures 6, 7:
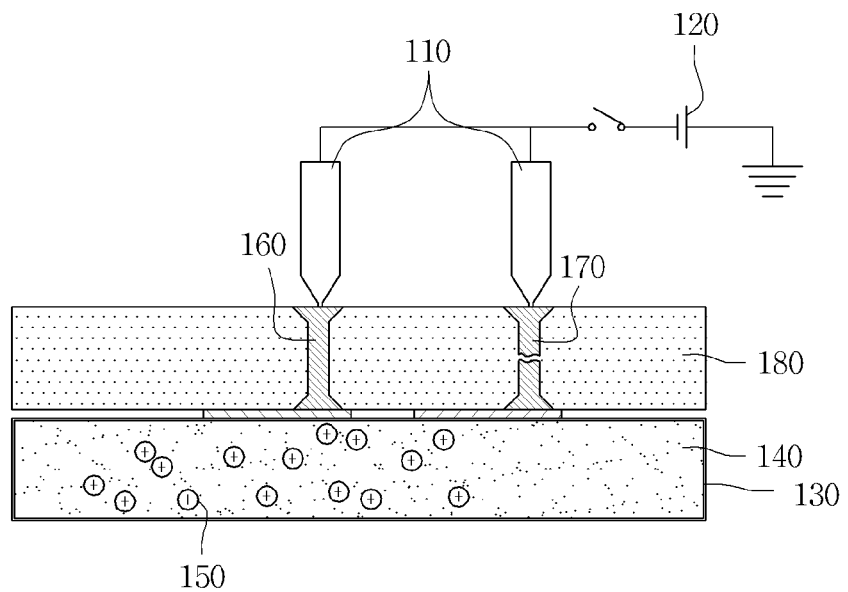
FIGS. 6 to 10 are sectional views sequentially showing a method of inspecting the circuit of a substrate according to an embodiment of the present invention.

First, as shown in FIG. 6, the pin probe 110 and the film 130, in which the dielectric fluid 140 in which the electronic ink 150 is dispersed, is sealed, are prepared. In this case, the specific gravities of the electronic ink 150 and the dielectric fluid 140 are preferably identical to each other. The reason for this is to use bi-stability at the time of determining, based on the flow of the electronic ink 150, whether the electrode 160 has been electrified in the subsequent procedure, which will be described later.

Next, as shown in FIG. 7, a pin probe 110 comes into contact with one end of each of the electrodes 160 and 170, formed on one side of the substrate 180, and the film 130 is disposed at the other end of each of the electrodes 160 and 170, formed on the other side of the substrate 180. In this case, the pin probes 110 preferably come into contact with the electrodes 160 and 170 to form an electric connection, and the film 130 is preferably located to fall within the range of an electric field that will be generated by the electrified electrode 160.

Figure 8:
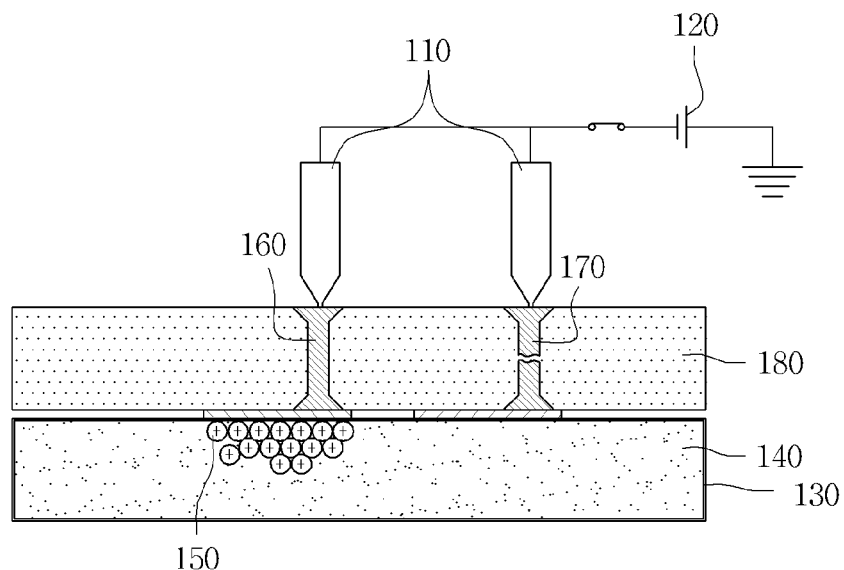
Figure 9:
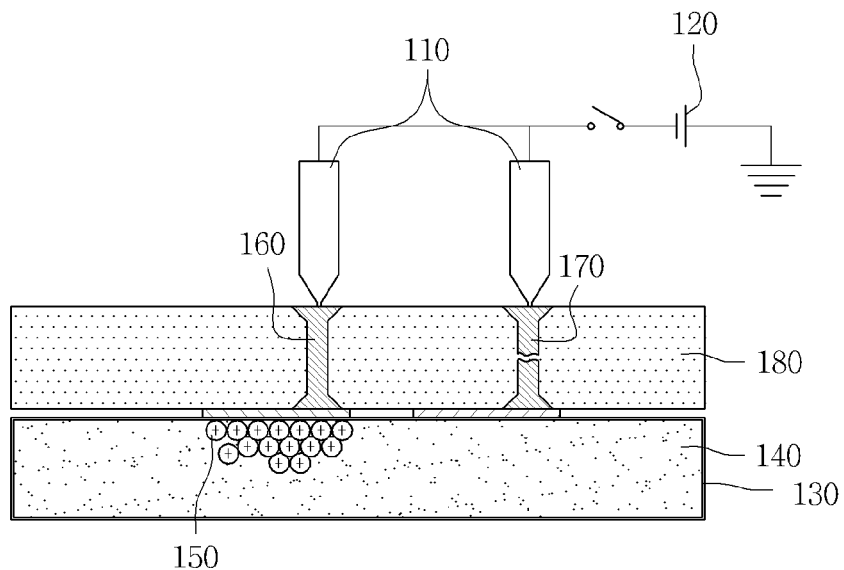
Figure 10:
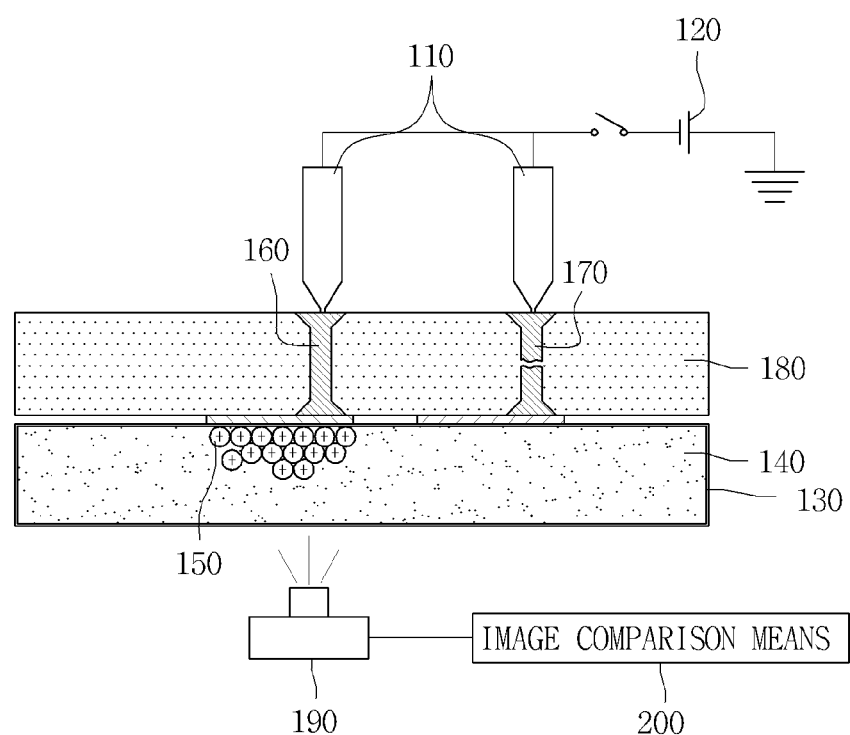

Next, as shown in FIGS. 8 to 10, whether the electronic ink 150, which is charged when the voltage source 120 applies a voltage to the pin probes 110, is flowing is measured, and thus whether the electrodes 160 and 170 have been electrified is determined. More preferably, this procedure includes applying a voltage to the pin probes 110, eliminating the voltage from the pin probes 110, and determining using the image comparison means 200 whether the electrodes 160 and 170 have been electrified, on the basis of measurements made using the camera 190.

First, referring to FIG. 8, the voltage source 120 applies the voltage to the pin probes 110. When the voltage is applied, the electronic ink 150 flows to the other end of the electrified electrode 160 due to electrical attractive force, and does not flow to the other end of the unelectrified electrode 170.

Next, referring to FIG. 9, the voltage applied to the pin probes 110 is eliminated When the flow of the electronic ink 150 stops, the voltage applied to the pin probes 110 is eliminated Even if the voltage is eliminated, the electronic ink 150 does not flow from the other end of the electrified electrode 160, owing to bi-stability. Therefore, the voltage source 120 needs only to selectively apply a voltage to the pin probes 110 only when the electronic ink 150 is flowing, and thus there is an advantage of reducing power consumption.

Next, referring to FIG. 10, whether the electrode 160 has been electrified is determined by the image comparison means 200, on the basis of measurements made using the camera 190. The flow of the electronic ink 150 can be determined by the naked eye, but an image indicating whether the electronic ink 150 is flowing is captured by the camera 190 so as to perform more precise measurement, and thus whether the electronic ink 150 is flowing can be better determined. Thereafter, the image captured by the camera 190 is transmitted to the image comparison means 200. In this case, a comparative image, obtained when the electrode is electrified (when the electrode is normal) is previously stored in the image comparison means 200. The image comparison means 200 compares the image captured by the camera 190 with the comparative image, and thus determines whether the electrode 160 has been electrified.

As described above, the present invention is advantageous in that whether an electrode has been electrified is measured using charged electronic ink, so that the use of pin probes is limited only to one side of a substrate, thus reducing the entire cost required for inspection.

Further, the present invention is advantageous in that, when defects in which an electrode pad has become slightly unfastened and then an electrode is not electrified are present, whether the electrode has been electrified is measured using electrophoresis by which a pressure is not applied, thus preventing the occurrence of erroneous measurements.

Furthermore, the present invention is advantageous in that, since pin probes need to come into contact with only one side of a substrate, measurement time is shortened, and in that, since current does not flow through the electrode, the breakdown of the electrode attributable to the generation of heat can be prevented.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The modifications or changes of the present invention belong to the scope of the present invention, and the detailed scope of the present invention will be more clearly understood by the accompanying claims.

What is claimed is:

1. An apparatus for inspecting a circuit of a substrate, comprising:
    a pin probe to come into contact with an end of an electrode exposed on a side of a substrate, the electrode being vertically formed through the substrate so as to be exposed relative to the substrate on the opposite side of the substrate;
    a voltage source for applying a voltage to the pin probe;
    a film disposed at the opposite end of the electrode on the opposite side of the substrate;
    dielectric fluid sealed in the film; and
    electronic ink dispersed in the dielectric fluid, and charged with electricity to flow when the electrode is electrified so as to permit electrical measurement of the electrode without a second pin probe coming into electrical contact with the electrode.

2. The apparatus as set forth in claim 1, wherein the film comprises a plurality of micro capsules, in which the dielectric fluid and the electronic ink are sealed.

3. The apparatus as set forth in claim 1, wherein the film comprises partitions which are vertically formed so that the electronic ink is separated at regular intervals.

4. The apparatus as set forth in claim 1, wherein the voltage source applies a positive voltage to the pin probe, and the electronic ink is charged with negative electricity.

5. The apparatus as set forth in claim 1, wherein the voltage source applies a negative voltage to the pin probe, and the electronic ink is charged with positive electricity.

6. The apparatus as set forth in claim 1, wherein the electronic ink includes white ink and black ink.

7. The apparatus as set forth in claim 6, wherein the white ink is charged with positive electricity and the black ink is charged with negative electricity.

8. The apparatus as set forth in claim 6, wherein the white ink is charged with negative electricity and the black ink is charged with positive electricity.

9. The apparatus as set forth in claim 1, wherein the film is made of polyethylene terephthalate (PET), poly carbonate (PC), polymethyl methacrylate (PMMA), polyethylene naphthalate (PEN), polyethersulfone (PES), cyclic olefin copolymer (COC), glass, or tempered glass.

10. The apparatus as set forth in claim 1, wherein the dielectric fluid is transparent.

11. The apparatus as set forth in claim 1, wherein the electronic ink and the dielectric fluid have identical specific gravities.

12. The apparatus as set forth in claim 1, further comprising a camera for capturing an image indicating whether the electronic ink is flowing.

13. The apparatus as set forth in claim 12, further comprising image comparison means for comparing the image captured by the camera with a comparative image, obtained when the electrode is electrified, thus determining whether the electrode has been electrified.

14. The apparatus as set forth in claim 1, wherein the substrate is a Printed Circuit Board (PCB) or a semiconductor wafer.

15. The apparatus as set forth in claim 1, wherein the opposite end of the electrode is connected to an electrode pad, the electrode pad being exposed on the opposite side of the substrate relative to the substrate; and the film is disposed at the electrode pad exposed on the opposite side of the substrate relative to the substrate.

16. A method of inspecting a circuit of a substrate, comprising:
(A) preparing a pin probe and a film in which dielectric fluid in which electronic ink is dispersed is sealed;
(B) bringing the pin probe into contact with an end of an electrode exposed on a side of a substrate and disposing the film at the opposite end of the electrode, the electrode exposed on the opposite side of the substrate relative to the substrate, the electrode being vertically formed thorough the substrate; and
(C) measuring whether the electronic ink, which is charged when a voltage source applies a voltage to the pin probe, is flowing without a second pin probe coming into electrical contact with the electrode, thus determining whether the electrode has been electrified.

17. The method as set forth in claim 16, wherein at (C), the electronic ink flows when the electrode is electrified.

18. The method as set forth in claim 16, wherein (C) is performed to capture an image using a camera, thus determining whether the electronic ink is flowing.

19. The method as set forth in claim 18, wherein (C) is performed to compare, using image comparison means, the image captured by the camera with a comparative image, obtained when the electrode is electrified, thus determining whether the electrode has been electrified.

20. The method as set forth in claim 16, wherein:
at (A), the electronic ink and the dielectric fluid have identical specific gravities; and
at (C), the voltage source applies the voltage to the pin probe only until flow of the electronic ink stops.

21. The method as set forth in claim 16, wherein the opposite end of the electrode is connected to an electrode pad, the electrode pad being exposed on the opposite side of the substrate relative to the substrate; and the film is disposed at the electrode pad exposed on the opposite side of the substrate relative to the substrate.

* * * * *